United States Patent
De Seixas Boavida Ferreira et al.

(10) Patent No.: US 9,382,300 B2
(45) Date of Patent: *Jul. 5, 2016

(54) **USE OF RECOMBINANT POLYPEPTIDES FROM THE GENUS *LUPINUS* AS ANTIMICROBIAL OR INSECTICIDAL ON PLANTS**

(71) Applicants: Ricardo Manuel De Seixas Boavida Ferreira, Lisbon (PT); Sara Alexandra Valadas Da Silva Monteiro, Lisbon (PT); Artur Ricardo Nascimento Teixeira, Oeiras (PT); Virgilio Borges Loureiro, Lisbon (PT)

(72) Inventors: Ricardo Manuel De Seixas Boavida Ferreira, Lisbon (PT); Sara Alexandra Valadas Da Silva Monteiro, Lisbon (PT); Artur Ricardo Nascimento Teixeira, Oeiras (PT); Virgilio Borges Loureiro, Lisbon (PT)

(73) Assignee: INSTITUTO SUPERIOR DE AGRONOMIA, Lisbon (PT)

( * ) Notice: Subject to any disclaimer, the term of this patent is extended or adjusted under 35 U.S.C. 154(b) by 0 days.

This patent is subject to a terminal disclaimer.

(21) Appl. No.: 13/965,590

(22) Filed: Aug. 13, 2013

(65) Prior Publication Data

US 2014/0007303 A1    Jan. 2, 2014

Related U.S. Application Data

(60) Division of application No. 12/893,889, filed on Sep. 29, 2010, now Pat. No. 8,541,654, which is a continuation-in-part of application No. 11/996,279, filed as application No. PCT/IB2006/052403 on Jul. 13, 2006, now Pat. No. 8,106,252.

(30) Foreign Application Priority Data

Jul. 21, 2005 (PT) .......................................... 103322
Jun. 28, 2006 (PT) .......................................... 103511

(51) Int. Cl.
*A01H 5/10* (2006.01)
*C07K 14/415* (2006.01)
*A01N 65/00* (2009.01)
*A01N 65/20* (2009.01)
*A23K 1/16* (2006.01)
*A23L 1/305* (2006.01)
*C12N 15/82* (2006.01)

(52) U.S. Cl.
CPC .............. *C07K 14/415* (2013.01); *A01N 65/00* (2013.01); *A01N 65/20* (2013.01); *A23K 1/1631* (2013.01); *A23L 1/3053* (2013.01); *C12N 15/8251* (2013.01); *C12N 15/8282* (2013.01)

(58) Field of Classification Search
None
See application file for complete search history.

(56) References Cited

U.S. PATENT DOCUMENTS 8,106,252 B2 *    1/2012   De Seixas Boavida Ferreira et al. ............................ 800/279

FOREIGN PATENT DOCUMENTS

EP    0316067 A2    5/1989

OTHER PUBLICATIONS

Office Action issued in corresponding European Patent Appln. No. 06780077.1 on Mar. 17, 2011, in the name of Instituto Superior de Agronomia, et al.
Response to Office Action (issued in corresponding European Patent Appln. No. 06780077.1), filed May 4, 2011 in the name of Instituto Superior de Agronomia et al.
"Beta-conglutin", Database UniProt [Online], retrieved from EBI Accession No. UNIPROT:Q6EBC1, Aug. 16, 2004.
"Vicilin-like protein (Fragment)", Database UniProt [Online], retreived from EBI Accession No. UNIPROT:Q53HYO, May 24, 2005.
Ricardo B. Ferreira et al., "The structure of Lupinus seed storage proteins. Recent developments", Current Topics in Plant Biology, 2003, 4:139-150.

* cited by examiner

*Primary Examiner* — Medina A Ibrahim
(74) *Attorney, Agent, or Firm* — Sughrue Mion, PLLC (57) ABSTRACT

This invention is related to a protein from the seeds, cotyledons or plantlets of *Lupinus* genus, as well as to the way of producing the protein in recombinant form and of expressing the protein in genetically modified plants. The invention relates to methods of its use, or of any modification of the protein that maintains its biological properties, as a supplement in human or animal nutrition and as a fungicide, insecticide, growth promoter, fertilizer or in the preparation of genetically modified organisms.

5 Claims, 7 Drawing Sheets
(6 of 7 Drawing Sheet(s) Filed in Color)

SEQUENCE LISTING

```
<160> NUMBER OF SEQ ID NOS: 3

<210> SEQ ID NO 1
<211> LENGTH: 173
<212> TYPE: PRT
<213> ORGANISM: Lupinus albus

<400> SEQUENCE: 1

Arg Arg Gln Arg Asn Pro Tyr His Phe Ser Ser Gln Arg Phe Gln Thr
1               5                   10                  15

Leu Tyr Lys Asn Arg Asn Gly Lys Ile Arg Val Leu Glu Arg Phe Asp
            20                  25                  30

Gln Arg Thr Asn Arg Leu Glu Asn Leu Gln Asn Tyr Arg Ile Val Glu
        35                  40                  45

Phe Gln Ser Lys Pro Asn Thr Leu Ile Leu Pro Lys His Ser Asp Ala
    50                  55                  60

Asp Tyr Val Leu Val Val Leu Asn Gly Arg Ala Thr Ile Thr Ile Val
65                  70                  75                  80

Asn Pro Asp Arg Arg Gln Ala Tyr Asn Leu Glu Tyr Gly Asp Ala Leu
                85                  90                  95

Arg Ile Pro Ala Gly Ser Thr Ser Tyr Ile Leu Asn Pro Asp Asp Asn
            100                 105                 110

Gln Lys Leu Arg Val Val Lys Leu Ala Ile Pro Ile Asn Asn Pro Gly
        115                 120                 125

Tyr Phe Tyr Asp Phe Tyr Pro Ser Ser Thr Lys Asp Gln Gln Ser Tyr
    130                 135                 140

Phe Ser Gly Phe Ser Arg Asn Thr Leu Glu Ala Thr Phe Asn Thr Arg
145                 150                 155                 160

Tyr Glu Glu Ile Gln Arg Ile Ile Leu Gly Asn Glu Asp
                165                 170

<210> SEQ ID NO 2
<211> LENGTH: 519
<212> TYPE: DNA
<213> ORGANISM: Lupinus albus

<400> SEQUENCE: 2
cgtagacaaa ggaaccctta tcacttcagc tctcaaagat tccaaactct ttacaaaaat      60
aggaatggca aaatccgtgt gctcgagagg tttgaccaaa gaaccaatag acttgagaat     120
ctccaaaact accgcattgt tgagttccaa tcaaaaccta acactctcat tctccctaaa     180
cactctgatg ctgactacgt cctcgttgta ctcaatggta gagccacaat cacgatagta     240
aaccctgata gaagacaagc atataacctt gagtatggcg atgctctcag aatcccagct     300
ggctcaactt catatatcct taacccggat gacaaccaga agcttagagt agtcaagctc     360 gcaatacccca tcaacaatcc tggctacttt tatgatttct atccatcgag tactaaagac     420
```

```
caacaatcct acttcagtgg cttcagcagg aacactttag aggccacctt caatactcgt      480
tatgaagaga tacaaaggat tattttaggg aatgaggat                             519

<210> SEQ ID NO 3
<211> LENGTH: 150
<212> TYPE: PRT
<213> ORGANISM: Lupinus albescens

<400> SEQUENCE: 3

Lys Ile Arg Val Leu Glu Arg Phe Asp Gln Arg Thr Asn Arg Leu Glu
1               5                   10                  15

Asn Leu Gln Asn Tyr Arg Ile Val Glu Phe Gln Ser Lys Pro Asn Thr
            20                  25                  30

Leu Ile Leu Pro Lys His Ser Asp Ala Asp Tyr Val Leu Val Val Leu
        35                  40                  45

Asn Gly Arg Ala Thr Ile Thr Ile Val Asn Pro Asp Arg Arg Gln Ala
    50                  55                  60

Tyr Asn Leu Glu Tyr Gly Asp Ala Leu Arg Ile Pro Ala Gly Ser Thr
65                  70                  75                  80

Ser Tyr Ile Leu Asn Pro Asp Asp Asn Gln Lys Leu Arg Val Val Lys
                85                  90                  95

Leu Ala Ile Pro Ile Asn Asn Pro Gly Tyr Phe Tyr Asp Phe Tyr Pro
            100                 105                 110

Ser Ser Thr Lys Asp Gln Gln Ser Tyr Phe Ser Gly Phe Ser Arg Asn
        115                 120                 125

Thr Leu Glu Ala Thr Phe Asn Thr Arg Tyr Glu Glu Ile Gln Arg Ile
    130                 135                 140

Ile Leu Gly Asn Glu Asp
145                 150
```

USE OF RECOMBINANT POLYPEPTIDES FROM THE GENUS *LUPINUS* AS ANTIMICROBIAL OR INSECTICIDAL ON PLANTS

CROSS REFERENCE TO RELATED APPLICATIONS

This is a Divisional of U.S. patent application Ser. No. 12/893,889, filed Sep. 29, 2010 (now U.S. Pat. No. 8,541,654), which is a Continuation-in-Part of U.S. patent application Ser. No. 11/996,279, filed Jan. 18, 2008 (now U.S. Pat. No. 8,106,252), which is a 371 National Stage Application of International Application No. PCT/IB2006/052403, filed Jul. 13, 2006, claiming priority to Portuguese Patent Application Nos. 103511 and 103322, filed Jun. 28, 2006 and Jul. 21, 2005. The entire disclosures of the prior applications are considered part of the disclosure and are hereby incorporated by reference.

FIELD OF THE INVENTION

This invention is included in the area of Biology, with its practical applicability as a fungicide, insecticide, growth promoter or fertilizer belonging to the fields of Agronomical Sciences and Agriculture and as its applicability as a supplement in the diet of animals belonging to the field of Human and Animal Nutrition.

BACKGROUND OF THE INVENTION

This invention relates to a polypeptide with antifungal, anti-Oomycete and plant growth promoter properties, extracted from seeds, cotyledons or plantlets of the genus *Lupinus*, and to its application in the control of pathogenic agents that attack plants and as a plant bio-stimulant. This polypeptide may be applied directly on plants, or the plants may be genetically modified to express the polypeptide in their tissues. In addition, due to its unusual inherent characteristics, the polypeptide may be utilized in the preparation of protein concentrates useful as supplements in the diet of man and other animals.

The present invention also describes the nucleotide DNA sequence corresponding to the gene fragment that encodes the *Lupinus* polypeptide, as well as its sequence of amino acid residues, microorganisms transformed with the gene fragment that encodes the *Lupinus* polypeptide and methods for its application as a fungicide, insecticide, plant growth promoter or fertilizer or as a supplement in human or animal nutrition.

It is also an object of this invention the polypeptide characterized by the sequence of amino acid residues referred above, in which one or more amino acid residues are absent, have been substituted or added, or maintaining its biological activities after suffering chemical modification, such as, for example, glycosylation.

The control of pathogenic agents constitutes a serious problem worldwide with respect to the most important crops. Pathogenic fungi are particularly important in what concerns the storage of agricultural products. Presently, control over fungal growth is generally achieved by massive applications of chemical fungicides. However, phytopharmaceutical products currently available in the market display several serious disadvantages. On one hand, they exhibit high economical and environmental costs; on the other hand, many fungal species have been developing resistance mechanisms to some top fungicides, often turning them obsolete in a couple of years after their introduction in the market.

Even though plants do not possess an immunological system resembling that of animals, they have evolved an inherent resistance to the attack of pathogenic fungi. However, the techniques employed for plant growth, harvest and storage in modern agriculture promote very often good or optimal conditions for pathogen development.

In addition, the number of microbial pathogens that may affect and harm plant crops is quite high. As an example, the following genera may be referred: *Alternaria, Ascochyta, Botrytis, Cercospora, Colletotrichum, Diplodia, Erysiphe, Fusarium, Gaeumanomyces, Macrophomina, Nectria, Phoma, Phomopsis, Phymatotrichum, Phytophthora, Plasmopara, Puccinia, Pythium, Rhizoctonia, Uncinula*, and *Verticillium*. The application of the fungicides currently available in the market is limited to some of these genera, and is not an effective solution in the control of plant infections.

An alternative strategy in the fight against microbial pathogens is the identification and purification of substances of biological origin with potent antifungal activity. The identification of such compounds involves searching a variety of organisms, such as plants and microorganisms, for substances that are subsequently tested in antifungal assays and finally isolated and characterized.

In this way, many classes of antifungal proteins have already been isolated, including chitinases, cystein-rich proteins that bind strongly to chitin, $\beta$-1,3-glucanases, permeatins, thionins and lipid transfer proteins. These proteins are thought to play a fundamental role in the natural defenses of plants against the attack of pathogens.

Several methodologies are described in the available literature on the utilization of antifungal proteins, extracted from plants or microorganisms, either for direct application over the pathogenic agents, or in transgenic plants expressing those proteins. The antifungal proteins most often utilized in these methodologies include chitinases, glucanases, osmotin-type proteins and lysozymes. Various studies have demonstrated that genetically modified plants over-expressing these proteins exhibit enhanced resistance to many pathogens (EP 0392 225).

Modern techniques of Molecular Biology allowed the development of recombinant DNA technology and, consequently, plant transformation with genes encoding antifungal proteins. This procedure usually involves insertion of the gene encoding the protein of interest in a plant tissue, followed by regeneration of a whole plant from the genetically modified plant tissue.

However, the activity of some of these proteins is reduced by the presence of ions, in particular potassium, sodium or calcium. For this reason, although the proteins may exhibit a potent antifungal activity in in vitro assays, they may be ineffective in vivo due to the high physiological concentrations of the ions that may naturally occur in the transformed plant tissues.

Document "Ramos, Paula Cristina Rodrigues, et. al—"Accumulation of a lectin-like breakdown product of beta-conglutin catabolism in cotyledons of germinating *Lupinus albus* L. seeds" *Planta* (Heidelberg), vol. 203, n° 1, 1997, pages 26-34" describes isolation and purification of a 20-kDa polypeptide which is an intermediate breakdown product of beta-conglutin catabolism, the vicilin-like storage protein, which interacts with a variety of glycoproteins and possesses a lectin-type activity. In Table 1 of this document, several N-terminal amino acid sequences are described including the one of the 20-kDa polypeptide isolated from *L. albus* seeds. However, the N-terminal sequence presented in the Table 1 of this document includes exclusively the identity of residues no. 5, 6, 7, 8, 9, 11, 12, 13, 14, 15, 16, 17, 18, 20, and 23. This corresponds to a total of 15 residues out of the 173 amino acid residues that compose SEQ ID NO: 1 of the present invention. In fact, the N-terminal sequence of this document is not the responsible for the biological properties related to the polypeptide of the present invention. Moreover, the N-terminal sequence described in the referred document is intended to be used to construct suitable primers, which may then be utilized in molecular biology as the first step of the long and uncertain process of gene and protein sequencing, while the main purpose of the present invention is to disclose a polypeptide exhibiting several biological activities.

The document "Database UniProt [Online] 16 Aug. 2004 (2004 Aug. 16)—"Beta-conglutin" discloses a protein obtained from *Lupinus albus*, namely beta-conglutin. This protein is the major seed storage protein present in *Lupinus* seeds. Despite being the precursor of the polypeptide with the sequence of SEQ ID NO:1, according to the present invention, these two polymers correspond to distinct molecules for a number of reasons, namely a) beta-conglutin is regarded as a protein, with a typical quaternary structure, whereas the molecule with the sequence of SEQ ID NO:1 should not be considered as a protein, but rather as a polypeptide; b) beta-conglutin, much like the vast majority of proteins, is easily destroyed by harsh conditions. On the opposite, the polypeptide of the present invention is extremely resistant to denaturation, withstanding prolonged boiling, treatment with strong acids or bases, detergents and organic solvents. In addition, it is resistant to the Sun ultraviolet radiation; c) these two molecules fulfil entirely different roles in nature—whereas beta-conglutin is a seed storage protein, the polypeptide of the present invention displays a protective role in the plant, exhibiting a potent antifungal activity and a growth promoter activity. On the other hand, whereas beta-conglutin possesses strong catalytic activities of chitosanase and chitinase, the polypeptide of the present invention exhibits catalytic activity of beta-N-acetyl-D-glucosaminidase and a low level of chitosanase activity.

Document "Database UniProt [Online] 24 May 2005 (2005 May 24)—"Vicilin-like protein (fragment)" discloses a fragment (length: 531 amino acid residues; molecular mass: 62,032 Da) of the same protein (i.e. beta-conglutin) described in the previous document (length: 533 amino acid residues; molecular mass: 62,130 Da). Therefore, all remarks made above in what concerns this document apply equally to the document under analysis.

In conclusion, it is becoming imperative the identification and purification of novel compounds of biological origin exhibiting anti-pathogen properties in the fight against the pathogens that affect plants. Particular importance must be given to those compounds that are effective over a wide range of pathogens and that maintain the biological activity under in vivo conditions.

Agricultural practices have been optimized, over a long time period, to promote plant growth and development and to increase crop production. On the other hand, it is predictable that in the medium to long term, food shortage may occur in many areas of the globe. Current techniques to control plant growth under environmentally controlled conditions are expensive and require complex equipment. For these reasons, many researchers have searched for and have reported physiologically active substances, either natural or synthetic, that exhibit a boosting effect upon the growth and development of crops. However, only a few of these substances have found practical application under real, agricultural conditions. Therefore, it is also increasingly important to discover or to develop plant growth promoters that are environmentally friend and that present no toxicity to man, animals and the environment.

Plant legumes or, more specifically, their seeds, are considered as the major source of protein worldwide for animal and human nutrition. In this respect, soybean fulfills a prominent role, not only for the high protein content and quality of its seeds, but also for their richness in oil. However, from the agricultural point of view, soybean requires fertile soils and an abundant water supply. Plants belonging to the *Lupinus* genus have conquered, over the last few decades, a relevant, strong and of great potential position in comparison to soybean. If, on one hand, their seeds possess protein and oil levels comparable to those of soybean, on the other, their species are well adapted to poor soils and to conditions of low water availability. For these reasons, lupins have sometimes been considered as the "poor cousins" of soybean.

The high level of alkaloids which are toxic to animals and which are naturally present in traditional, wild-type lupin seeds have long hampered the generalized cultivation of *Lupinus* species and the use of their seeds for animal and human consumption. This is the main reason why lupin cultivation has lagged far behind that of soybean. In Portugal, for example, traditional consumption of lupin seeds has long been associated to beer ingestion. These seeds are first boiled in water (heating at 100° C. destroys the capacity of seeds to germinate but does not block the imbibition's process) and then immersed under running water for a few days to remove the toxic alkaloids. However, the recent application of breeding techniques allowed the development of the so called sweet lupin varieties, characterized by containing a low seed alkaloid content (<0.004% w/w), as opposed to the traditional bitter cultivars (alkaloid content >0.004% w/w). For this reason, the seeds of sweet lupin varieties may be safely utilized as human and animal feed.

It is therefore predictable an increasing development of lupin-derived food products for both human and animal nutrition, as has happened a number of decades ago with soybean. This is particularly important in the case of lupin seed proteins, either albumins or globulins.

SUMMARY OF THE INVENTION

It is expected for the present invention to solve the technical problem associated with the identification and purification of compounds of biological origin that are capable of controlling a wide range of pathogenic agents that affect plant crops and that act as plant growth promoters while maintaining their biological activities under in vivo conditions.

The solution is based on the characterization and identification of a polypeptide present in plants belonging to the genus *Lupinus*, that exhibits the following unusual characteristics: (i) a potent antifungal and anti-Oomycete activity, which confers great potential as a fungicide; (ii) a strong plant growth promoter activity, particularly notorious on unhealthy or naturally weakened plants; (iii) an extreme resistance to denaturation, allowing its use under field conditions; (iv) a very high susceptibility to proteolysis, which makes it harmless to the environment and nontoxic to man and animals; and (v) a well balanced amino acid composition.

Therefore, the first aspect of the present invention refers to the polypeptide with the sequence: (5' KIRVLER FDQRTNRLEN LQNYRIVEFQ SKPNTLILPK HSDADYVLVV LNGRATITIV NPDRRQAYNL EYGDALRIPA GSTSYIL-NPD DNQKLRVVKL AIPINNPGYF YDFYPSSTKD QQSYFSGFSR NTLEATFNTR YEEIQRIILG NED 3') (SEQ ID NO: 3).

Another aspect of the invention refers to the polypeptide with the sequence of SEQ ID NO: 1

Another aspect of the present invention concerns a DNA fragment that encodes that polypeptide. The invention also regards the use of the polypeptide, or any preparation containing it, as a fungicide, insecticide, growth promoter or fertilizer, either by direct application, in recombinant form or by expression in genetically modified organisms. Finally, the invention considers the use of the polypeptide or any preparation containing it as a supplement in human or animal nutrition.

BRIEF DESCRIPTION OF DRAWINGS

The patent or application file contains at least one drawing executed in color. Copies of this patent or patent application publication with color drawing(s) will be provided by the Office upon request and payment of the necessary fee.

DETAILED DESCRIPTION OF THE INVENTION

The present invention refers to a novel polypeptide with potent antifungal properties, which exhibits a powerful activity on the germination and development of spores from fungal and Oomycete pathogens for plants, and with plant growth promoter activity, particularly notorious on unhealthy or naturally weakened plants. The invention also considers the use of the polypeptide or any preparation containing it as a supplement in human or animal nutrition. The DNA nucleotide sequence of the gene fragment that encodes the polypeptide from *Lupinus* does not share any significant homology with any other antifungal protein/polypeptide that has been isolated from plants. The polypeptide from *Lupinus* constitutes a novel type of polypeptide among the antifungal proteins described in plants.

The polypeptide referred to in the present invention is purified from cotyledons extracted from germinated seedlings of the genus *Lupinus*. The present invention includes the description of the methodology employed to isolate the polypeptide from the plant tissues, the DNA nucleotide sequence of the gene fragment (SEQ ID NO: 2) that encodes it, and the corresponding sequence of amino acid residues (SEQ ID NO: 1). The carboxy terminal region of the polypeptide is represented by SEQ ID NO: 3.

(SEQ ID NO: 1)

Arg Arg Gln Arg Asn Pro Tyr His Phe Ser Ser Gln Arg Phe Gln Thr

Leu Tyr Lys Asn Arg Asn Gly Lys Ile Arg Val Leu Glu Arg Phe Asp

Gln Arg Thr Asn Arg Leu Glu Asn Leu Gln Asn Tyr Arg Ile Val Glu

Phe Gln Ser Lys Pro Asn Thr Leu Ile Leu Pro Lys His Ser Asp Ala

Asp Tyr Val Leu Val Val Leu Asn Gly Arg Ala Thr Ile Thr Ile Val

Asn Pro Asp Arg Arg Gln Ala Tyr Asn Leu Glu Tyr Gly Asp Ala Leu

Arg Ile Pro Ala Gly Ser Thr Ser Tyr Ile Leu Asn Pro Asp Asp Asn

Gln Lys Leu Arg Val Val Lys Leu Ala Ile Pro Ile Asn Asn Pro Gly

Tyr Phe Tyr Asp Phe Tyr Pro Ser Ser Thr Lys Asp Gln Gln Ser Tyr

Phe Ser Gly Phe Ser Arg Asn Thr Leu Glu Ala Thr Phe Asn Thr Arg

-continued

Tyr Glu Glu Ile Gln Arg Ile Ile Leu Gly Asn Glu Asp (SEQ ID NO: 2)

5'CGTAGACAAAGGAACCCTTATCACTTCAGCTCTCAAAGATTCCAAACTCTTTACAAAAATA

GGAATGGCAAAATCCGTGTGCTCGAGAGGTTTGACCAAAGAACCAATAGACTTGAGAATCTCC

AAAACTACCGCATTGTTGAGTTCCAATCAAAACCTAACACTCTCATTCTCCCTAAACACTCTG

ATGCTGACTACGTCCTCGTTGTACTCAATGGTAGAGCCACAATCACGATAGTAAACCCTGATA

GAAGACAAGCATATAACCTTGAGTATGGCGATGCTCTCAGAATCCCAGCTGGCTCAACTTCAT

ATATCCTTAACCCGGATGACAACCAGAAGCTTAGAGTAGTCAAGCTCGCAATACCCATCAACA

ATCCTGGCTACTTTTATGATTTCTATCCATCGAGTACTAAAGACCAACAATCCTACTTCAGTG

GCTTCAGCAGGAACACTTTAGAGGCCACCTTCAATACTCGTTATGAAGAGATACAAAGGATTA

TTTTAGGGAATGAGGAT3'

(SEQ ID NO: 3)

5'KIRVLER FDQRTNRLEN LQNYRIVEFQ SKPNTLILPK HSDADYVLVV

LNGRATITIV NPDRRQAYNL EYGDALRIPA GSTSYILNPD DNQKLRVVKL

AIPINNPGYF YDFYPSSTKD QQSYFSGFSR NTLEATFNTR YEEIQRIILG NED 3'

This polypeptide appears to occur naturally during only a very short period in the lifetime of plantlets from *Lupinus* genus. It has been demonstrated by the present inventors that β conglutin, the major seed storage protein from *Lupinus* genus, is the biosynthetic precursor of the polypeptide from *Lupinus*. Indeed, the *Lupinus* polypeptide is a highly processed polymer that has undergone several levels of chemical modification. This increased tremendously the difficulty of its study, including the sequencing of amino acid residues and of the corresponding nucleotides. During seed formation, the gene encoding β conglutin is transcribed into the corresponding mRNA, whose translation results in the synthesis of the biosynthetic precursor of β conglutin. This precursor is then extensively processed, including glycosylation, from which the several tens of different types of subunits that compose β conglutin are produced. In the following cycle of vegetative growth, several days after the onset of germination, the initial steps in the catabolism of β conglutin involve proteolytic cleavage of all or most of its constituent subunits, resulting in the accumulation of a native protein, as the major subunit, corresponding to the polypeptide described in this invention. Due to its intrinsic antifungal properties, which are naturally exploited by the host plant, this polypeptide is maintained in very high concentrations in the cotyledons of the developing plants, during a life stage in which the plant is most sensitive to fungal and insect attack. After a few days, the polypeptide is degraded and its amino acids used in the growth of the young plant.

The *Lupinus* polypeptide described in the present invention exhibits some properties that distinguish it from the other antifungal proteins described in the literature. This makes it a promising target with great potential to develop an efficient method to control the fungi that affect plants and/or animals:
(1) Potent antifungal and anti-Oomycete activity, which confers great potential to the polypeptide as a fungicide,
(2) Strong plant growth promoter activity, particularly notorious on unhealthy or naturally weakened plants,
(3) Extreme resistance to denaturation, which allows the use of the polypeptide under field conditions,
(4) Great susceptibility to proteolytic attack, which makes it harmless to the environment and nontoxic for man, and
(5) A well-balanced amino acid composition.

The polypeptide may also be utilized as an insecticide, growth promoter or fertilizer, and as a food supplement in human or animal nutrition.

In one embodiment, the polypeptide of the invention has the amino acid sequence of SEQ ID NO:1 wherein one or more amino acid residues are deleted, substituted, added or modified, and the polypeptide maintains antifungal, anti-Oomycete, insecticidal or plant growth promoting activity. In one embodiment, the polypeptide is represented by a sequence having not more than 50 deleted, substituted, added or modified amino acid residues to SEQ ID NO: 1, such as not more than 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, or 49 amino acid residues are deleted, substituted, added or modified.

In one embodiment, the polynucleotide of the invention has a modified sequence in which one or more nucleotides are deleted, substituted, added or modified, and which encodes a polypeptide with antifungal activity, anti-Oomycete activity, insecticidal or plant growth promoter activity. In one embodiment, the polynucleotide is represented by a sequence having not more than 50 deleted, substituted, added or modified nucleotides to SEQ ID NO: 2, such as not more than 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, or 49 nucleotides are deleted, substituted, added or modified.

Sequence identity: The similarity between amino acid sequences or between nucleic acid sequences can be expressed in terms of the percentage of conservation between the sequences, referred to as sequence identity. Sequence identity is frequently measured in terms of percentage identity (or similarity or homology); the higher the percentage, the more similar the two sequences are. In one embodiment, homologues or variants encompassed by the invention will possess a relatively high degree of sequence identity when aligned to SEQ ID NOs: 1 or 2 using standard methods.

Methods of alignment of sequences for comparison are well known in the art. Various programs and alignment algorithms are described in: Smith and Waterman, Adv. Appl. Math. 2:482, 1981; Needleman and Wunsch, J. Mol. Biol.

48:443, 1970; Pearson and Lipman, Proc. Natl. Acad. Sci. U.S.A. 85:2444, 1988; Higgins and Sharp, Gene 73:237, 1988; Higgins and Sharp, CABIOS 5:151, 1989; Corpet et al., Nucleic Acids Research 16:10881, 1988; and Pearson and Lipman, Proc. Natl. Acad. Sci. U.S.A. 85:2444, 1988. Altschul et al., Nature Genet., 6:119, 1994, presents a detailed consideration of sequence alignment methods and sequence identity calculations.

The NCBI Basic Local Alignment Search Tool (BLAST) (Altschul et al., J. Mol. Biol. 215:403, 1990) is available from several sources, including the National Center for Biotechnology Information (NCBL Bethesda, Md.) and on the NCBI website on the Internet, for use in connection with the sequence analysis programs blastp, blastn, blastx, tblastn and tblastx. A description of how to determine sequence identity using this program is available on the NCBI website. Other specific, non-limiting examples of sequence alignment programs specifically designed to identify conserved regions of genomic DNA of greater than or equal to 100 nucleotides are PIPMaker (Schwartz et al., Genome Research 10:577-586, 2000) and DOTTER (Erik et al., Gene 167:GC1-10, 1995).

In one embodiment, the polypeptide of the invention has a sequence of at least 75% sequence identity to the sequence set forth in SEQ ID NO: 1, such as, but not limited to at least 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 99.9% sequence identity to the polypeptide set forth in SEQ ID NO: 1.

In one embodiment, the polynucleotide of the invention has a sequence at of least 75% identity to the sequence set forth in SEQ ID NO: 2, such as, but not limited to at least 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 99.9% sequence identity to the polynucleotide set forth in SEQ ID NO: 2.

In one embodiment, homologues and variants of SEQ ID NOs: 1 and 2 encompassed by the invention are typically characterized as having a percentage sequence identity counted over the full length alignment with the corresponding sequence of SEQ ID NOs: 1 or 2 using, in one embodiment, the NCBI Blast 2.2.23, set to default parameters. Methods for determining sequence identity over short windows are available at the NCBI website on the Internet. One of skill in the art will appreciate that these sequence identity ranges are provided for guidance only; it is entirely possible that strongly significant homologues could be obtained that fall outside of the ranges provided.

In another embodiment, the peptide of the invention has not more than 50 conservative substitutions to SEQ ID NO: 1, such as not more than 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, or 49 conservative substitution are present.

Two practical problems in present-day agriculture are the growth reduction or inhibition observed in unhealthy or naturally weakened plants and the toxicity normally associated to available bio-stimulants. The polypeptide extracted from *Lupinus* plant tissues exhibits a strong growth promoter activity upon plant growth and development. Indeed, *Lupinus* preparations or extracts containing the polypeptide possess a strong bio-stimulatory activity upon all tested plants, including, for example, grapevine, rose, watermelon and tomato. This effect is notorious for concentrations of the native protein containing the polypeptide equal to or above 200 µg/mL. The other components present in non-pure extracts of the *Lupinus* polypeptide add value to the preparations because they act as a foliar fertilizer. The absence of toxicity of the *Lupinus* polypeptide for man, animals and the environment indicate that its applications in agriculture do not have any damaging effect on the environment.

Another aspect of the present invention concerns the methodology utilized for the recombinant production of the *Lupinus* polypeptide in bacteria, with the aim of expressing it constitutively in genetically modified plants. Eventually, these plants will present a high level of resistance to pathogenic fungi, namely with respect to the fungi of difficult control (as is the case of the fungi responsible for the so called wood diseases), against which the traditional fungicides of exogenous application are not at all effective.

The polypeptide was extracted from eight-days-old *Lupinus albus* cv. LeBlanc pantlets. The seeds were placed in a constant temperature room (25° C. day, 20° C. night) with a photoperiod of 16 h light/8 h dark.

After harvest, the cotyledons were frozen in liquid nitrogen. polypeptide extraction was performed in 100 mM Tris-HCl buffer, pH 7.5, containing 10% (w/v) NaCl, 10 mM EDTA (ethylenediamine-tetraacetic acid) and 10 mM EGTA (ethylene glycol bis((3-aminoethyl ether)-N,N,N',N'-tetraacetic acid). After an incubation period of 30 minutes at 4° C., the extract was centrifuged at 30,000 g, for 1 h at 4° C. The supernatant was desalted and the native protein containing the polypeptide extracted from *Lupinus* subsequently purified by FPLC (Fast Protein and Peptide Liquid Chromatography)-anion exchange chromatography.

N-terminal sequencing of the polypeptide extracted from *Lupinus* was accomplished by Edman degradation. The obtained sequence of amino acid residues was used to design degenerate primers. Total mRNA was extracted from developing *Lupinus albus* seeds at a stage where maximal synthesis of the β conglutin precursor occurs. The mRNA extraction was performed using protocols/kits for mRNA purification from plant material. The cDNA corresponding to the gene fragment encoding the polypeptide extracted from *Lupinus* was amplified by PCR (polymerase chain reaction) using the degenerate primers previously designed. Using the nucleotide sequence obtained as a template, new primers were designed and the complete nucleotide sequence of the gene fragment encoding the polypeptide extracted from *Lupinus* was achieved by the 3' and 5' RACE (rapid amplification of cDNA ends) technique.

The polypeptide from *Lupinus* was produced in recombinant form in the bacterium *Escherichia coli*. The gene fragment encoding the polypeptide from *Lupinus* was cloned in a suitable vector, allowing the association of the gene of interest to the promoter T7lac. This promoter is inductive; therefore, the expression of the genes that are associated with it occurs exclusively in the presence of the sugar isopropylthio-β-galactoside. Finally, competent *Escherichia coli* cells were transformed.

As described above, the polypeptide from *Lupinus* was obtained in a recombinant form from bacteria. However, to be tested for its antifungal activity, the recombinant polypeptide from *Lupinus* had to be isolated from all other bacterial proteins/polypeptide. To this end, the polypeptide from *Lupinus* was previously produced in a recombinant form with a tag of histidine residues (His-Tag). The methodology employed for its purification was based on the high affinity of the nickel ions for the His-Tag. In this way, having nickel ions bound to an agarose matrix, the purification of the recombinant polypeptide was accomplished knowing that among all the proteins/polypeptide present in the bacterial total extract, only the polypeptide from *Lupinus* binds to the agarose matrix. Subsequently, the polypeptide from *Lupinus* was recovered after a suitable set of washes and elutions, and the His-Tag removed after treatment with an appropriate proteolytic enzyme.

The careful choice of a suitable promoter is a pre-requisite for plant genetic modification. Several types of promoters are described in the literature, allowing the expression of the associated genes. To express the gene fragment encoding the polypeptide described in the present invention, the selected promoter may be inductive or constitutive, depending on the type of expression required. The choice of the promoter is also important to direct the synthesized polypeptide to the tissue or cellular compartment selected (post-transcriptional modifications).

Plant transformation may be achieved by different methodologies, such as, for example, plant transformation via *Agrobacterium*, protoplast transformation, gene transfer to pollen grains, direct injection into reproductive organs or immature embryos, and particle bombardment. Each of these methods presents specific advantages and disadvantages. Nevertheless, they all have already been utilized in different plant types.

Figure 1:
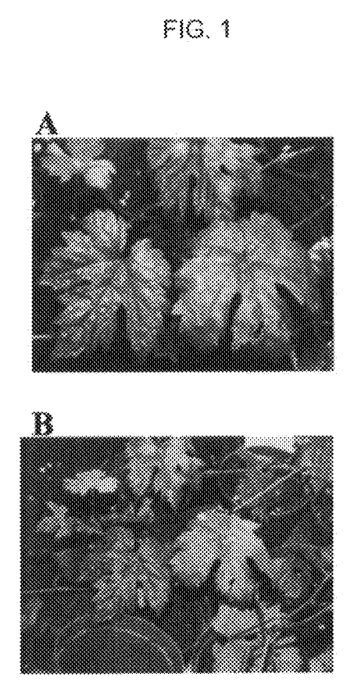
FIG. 1—Grapevine leaves heavily infected with powdery mildew were sprayed with water (leaf on the right) or with the native protein containing the polypeptide extracted from *Lupinus* (leaf on the left). (A) 24 h after spraying; (B) 2 months after spraying.
Figure 2:
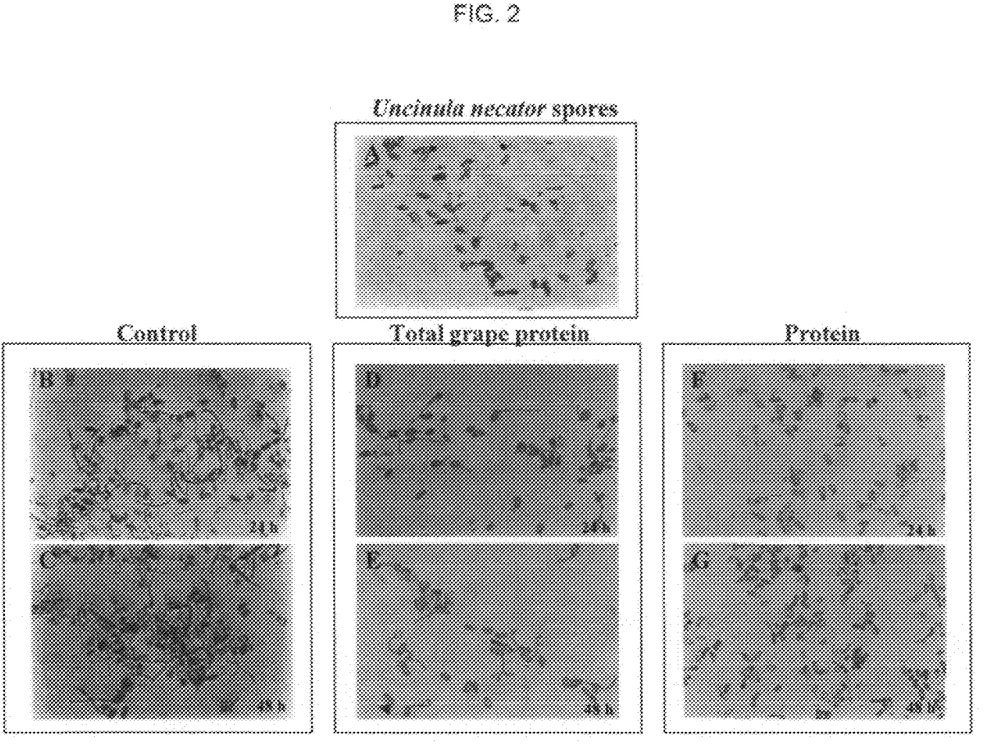
FIG. 2—Optical microscopy observations of germination of spores from the fungus responsible for powdery mildew in grapevine. Fungal spores were carefully removed from the surface of young infected grapevine leaves and inoculated in water agar 0.6% (w/v). (A), (B) and (C)—Controls; (D) and (E)—addition of 200 μg of the total protein fraction from mature grapes, containing pathogenesis-related (PR) proteins; (F) and (G)—addition of 200 μg of the native protein containing the polypeptide extracted from *Lupinus*. Each assay was observed after 24 and 48 h. Phase contrast microscopy was employed and the magnification used was 125×.
Figure 3:
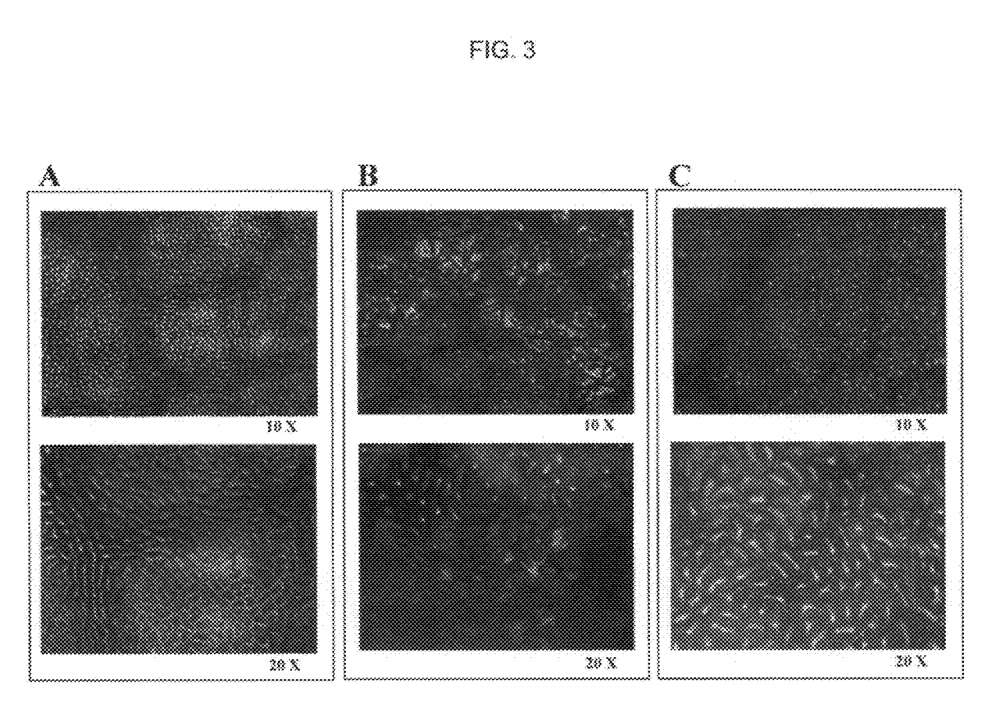
FIG. 3—Metallurgic microscopic observations of grapevine leaves. (A) Healthy leaves; (B) leaves infected with powdery mildew; (C) leaves infected with powdery mildew, 12 h after spraying with the native protein containing the polypeptide extracted from *Lupinus*. The magnification used is specified in each photograph.

To transform plants with the gene fragment encoding the polypeptide from *Lupinus*, the selected method was transformation via *Agrobacterium* (Fraley et al., 1983), using a suitable expression vector, containing a codifying region for the gene of interest associated to an appropriate marker gene. Plant regeneration, plant development and plant transfer to the culture medium from a single protoplast may be achieved following several methodologies available in the literature. This process includes several steps on the selection of transformed cells and the subsequent culture of these cells by the usual methods employed in the development of embryogenic cultures. The regenerated plantlets are finally grown in a suitable culture medium, usually soil.

It is also object of the present invention any agricultural formulation that includes as the active ingredient the polypeptide with the sequence of SEQ ID NO: 1, glycosylated, phosphorylated, alkylated and/or prenylated, or a recombinant form of the polypeptide obtained by transformation of cells characterized by being utilized in prevention, control and fight of pathogenic fungi or Oomycetes or plagues caused by insects, or as a growth promoter or fertilizer.

Another aspect of the present invention is related to the frequent reduced levels in plant proteins/polypeptides of the human and animal diets and, in some cases, to the poor protein digestibility and an imbalanced amino acid composition. In fact, crude preparations containing the *Lupinus* polypeptide possess not only a major globulin (the *Lupinus* native protein containing the polypeptide, object of the present invention) but also a variety of albumins that are naturally present in the plant material utilized in the protein extraction. Therefore, these crude preparations of the *Lupinus* polypeptide are particularly rich in proteins and may be utilized as a protein supplement in animal or human nutrition as tofu (after globulin precipitation with calcium and magnesium) or as ricotta (after heat precipitation of the albumins).

The analysis of the amino acid composition of the *Lupinus* polypeptide and its great susceptibility to all tested proteases (including trypsin, chymotrypsin, subtilisin, proteinase K and pronase) indicate that this polypeptide has a high nutritive value for animals. However, the polypeptide considered in the present invention is a globulin. For this reason, the *Lupinus* polypeptide or the native protein containing it are insoluble in water and in dilute salt solutions, but readily soluble in high ionic strength solutions. Nevertheless, legume globulins are insoluble only when in the presence of calcium, magnesium and other alkaline-earth cations (Ferreira et al., 1999). These divalent cations, positively charged at neutral pH values, act as electrostatic bridges between negatively charged globulin molecules, promoting or inducing their self-aggregation into complexes that are so large that are insoluble (Ferreira et al., 1999; Ferreira et al., 2003). Tofu, for example, is a curd similar to cheese or cottage cheese prepared by adding calcium and magnesium ions to a heated extract of soya beans. Both cations are routinely utilized in tofu preparation and are commercially available in the form of Nigari®. In this way, a crude preparation of the *Lupinus* polypeptide, containing both globulins and albumins, may be used in the preparation of *Lupinus* globulin concentrates after their precipitation with calcium and/or magnesium. FIG. 7, for example, shows the precipitation pattern of the *Lupinus* native protein containing the polypeptide (■) as a function of added calcium and magnesium concentrations. For comparative purposes, it is also presented the precipitation profile of its precursor protein, β-conglutin (the main storage protein present in *Lupinus* seeds; ○). The albumins that remain in the resulting serum may also be recovered, for example, by heat precipitation, in a process similar to that utilized in the preparation of ricotta (heat precipitation of the milk albumins that remain in the serum after casein removal during cheese making). In this way, preparations containing the *Lupinus* polypeptide may be utilized as a protein supplement in the human or animal diet.

To understand the potential of the present invention, several practical examples follow. However, these examples are not limiting in the sense that alternative methodologies may be employed in the utilization of the polypeptide from *Lupinus* as an agent of antifungal and Oomycete control, as an insecticide, as a growth promoter, as a fertilizer or as a protein supplement in the human or animal diet.

PRACTICAL EXAMPLES

Examples 1 and 2

Effect of spraying the native protein containing the polypeptide from *Lupinus* on the surface of grapevine leaves infected with the fungus *Uncinula necator* (the causal agent of powdery mildew in grapevine).

The antifungal activity of the polypeptide from *Lupinus* was evaluated after spraying the surface of a grapevine leaf with a solution containing 200 μg of pure native protein containing the polypeptide/mL. As a control, a similar leaf was sprayed under identical conditions with water. The results obtained are presented in FIG. 1 and show that the grapevine leaf remains healthy two months after spraying the leaves with the native protein containing the polypeptide, without traces of the fungus presence, even though the sprayed leaves were always and permanently kept in close contact with heavily infected leaves.

Another trial was performed following an identical methodology, but the observations of the surfaces of the treated grapevine leaves were made using a metallurgic microscope (FIG. 3).

Example 3

Effect of the native protein containing the polypeptide from *Lupinus* on the germination and development of spores from *Uncinula necator.*

Spores from the fungus *Uncinula necator* were removed from the surface of infected grapevine leaves and inoculated in water agar 0.6% (w/v), containing 200 μg of pure native protein containing the polypeptide from *Lupinus* per mL, or 200 μg of the total protein fraction from mature grapes (containing PR proteins) per mL. Spore germination and development of the germ tubes were followed by optical microscopy using the contrast phase lens system, during 24 and 48 h. The results obtained, presented in FIG. 2, show that a marked reduction occurred in the presence of the medium containing the polypeptide from *Lupinus*, not only in the number of germinated spores, but also in the length of the germ tubes. This effect is notorious when compared with the result observed in the presence of the PR proteins.

Example 4

Effect of the native protein containing the polypeptide from *Lupinus* on the germination and development of spores from the fungus *Phomopsis viticola* (the causal agent of excoriosis in grapevine).

Spores from the fungus *Phomopsis viticola* were inoculated in PDA (potato dextrose agar) medium. After 15 minutes, the spores were removed and mixed with a solution containing the native protein containing the polypeptide from *Lupinus* in a final volume of 25 µL. These droplets were placed in Petri dishes and overlaid with glass slides which were subsequently sealed, creating a wet chamber. Spore development was followed by optical microscopy observations. A clear inhibition of spore germination was evident. After 24 h developing hyphae suffered lysis.

Example 5

Effect of the recombinant polypeptide from *Lupinus* on the germination of spores from the fungus *Uncinula necator*.

Figure 4:
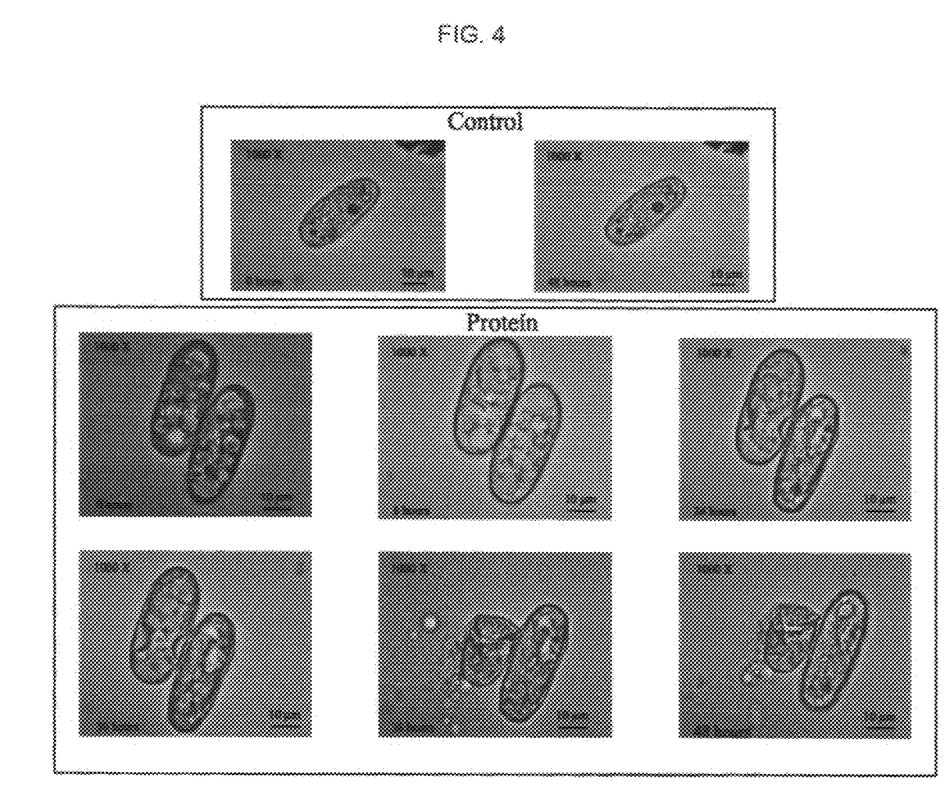
FIG. 4—Effect of the polypeptide from *Lupinus*, produced in a recombinant form in *Escherichia coli*, on the germination and development of *Uncinula necator* spores, the causal agent of powdery mildew.

The recombinant polypeptide from *Lupinus*, expressed in bacteria, was purified and its antifungal activity tested. These assays were performed as previously described in examples 2 and 3. The results obtained, presented in FIG. 4, show that the recombinant polypeptide exhibit identical antifungal properties to those observed for the polypeptide extracted from *Lupinus* plants. After a 48 h incubation period in the presence of the recombinant polypeptide from *Lupinus*, destruction of the spore cell walls is observed.

Example 6

Effect of the recombinant polypeptide from *Lupinus* on the germination of spores from the Oomycete *Plasmopara viticola* (the causal agent of downy mildew).

Spores from the Oomycete *Plasmopara viticola* were removed from the surface of grapevine infected leaves and placed in water agar 0.6% (w/v), containing 200 µg of recombinant pure polypeptide from *Lupinus* per mL. Spore germination was followed during 48 h by optical microscopy observations. Spore germination in water agar was used as a control. After 24 h, the spore cell walls were destroyed, with the concomitant release of the cellular content.

Example 7

Effect of spraying the native protein containing the polypeptide extracted from *Lupinus* on rose plants.

Figure 5:
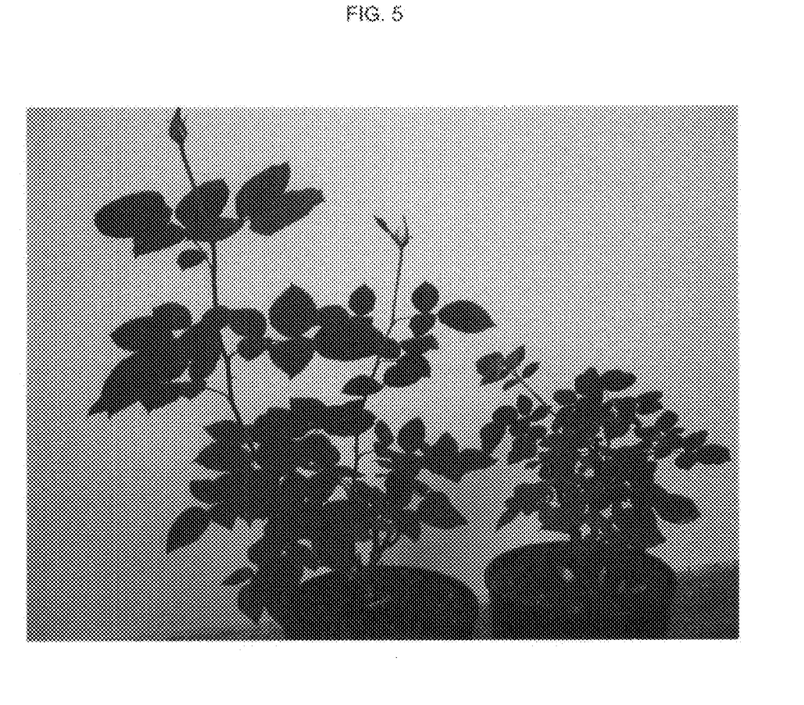
FIG. 5—Rose plants in the same developmental stage were sprayed with water (rose plant on the right) or with a solution containing the polypeptide extracted from *Lupinus* (200 μg native protein containing the polypeptide/mL; rose plant on the left). The photograph shows the developmental stage of both plants three weeks after spraying.

The bio-stimulant activity of the *Lupinus* native protein containing the polypeptide was evaluated after spraying the leaf surfaces of a rose plant with a crude *Lupinus* extract containing 200 µg native protein containing the polypeptide/mL. As a control a rose plant in an identical developmental stage and incubated under the same environmental conditions was sprayed with water. The result obtained, photographed three weeks after spraying, is presented in FIG. 5 and shows a superior growth for the plant sprayed with the *Lupinus* polypeptide, evidencing a premature appearance of the first floral buds.

Example 8

Effect of spraying the native protein containing the polypeptide extracted from *Lupinus* on nursery watermelon plants.

Figure 6:
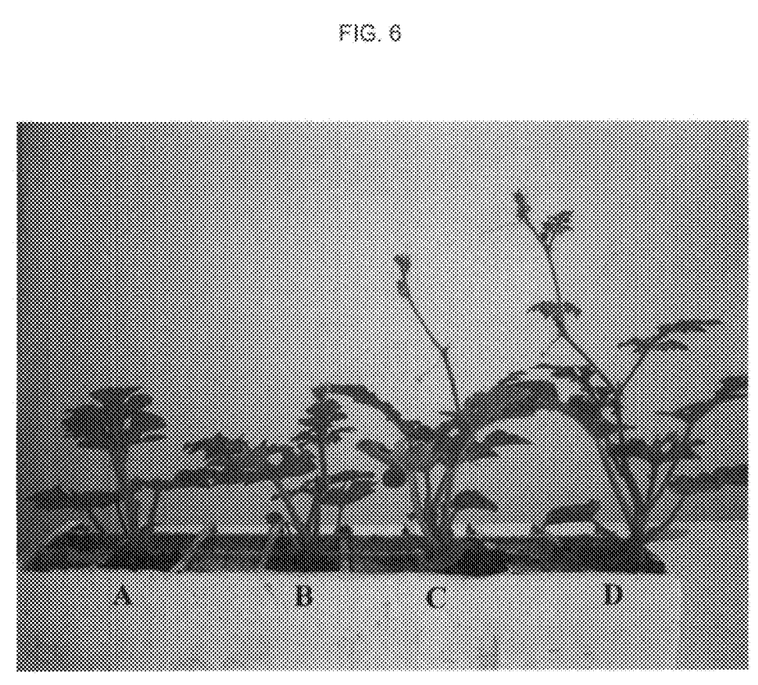
FIG. 6—Watermelon plants produced in a nursery. Six weeks after the onset of germination the plants were sprayed with water (control; A), a crude *Lupinus* extract containing 100 μg native protein containing the polypeptide/mL (B), a plant growth promoter commercially available in the market (concentration recommended by the manufacturer) (C), and a crude *Lupinus* extract containing 200 μg native protein containing the polypeptide/mL (D). The experiment was followed during two weeks and the plants photographed.

The bio-stimulant activity of the *Lupinus* polypeptide was evaluated after spraying the leaf surfaces of six-weeks-old nursery watermelon plants with a crude *Lupinus* extract containing 200 µg native protein containing the polypeptide/mL. The assay was performed under greenhouse conditions and the plants were sprayed with water (control; A); a crude *Lupinus* extract containing 100 µg native protein containing the polypeptide/mL (B); a plant growth promoter commercially available in the market (concentration recommended by the manufacturer) (C); and a crude *Lupinus* extract containing 200 µg native protein containing the polypeptide/mL (D). Twenty-four plants were used in each assay. The assay was followed during the subsequent two weeks and the results obtained are presented in FIG. 6. The plants sprayed with the highest concentration of the *Lupinus* polypeptide (200 µg native protein containing the polypeptide/mL; D) exhibit the greatest development and a superior leaf growth when compared with plants treated with water or with the plant growth promoter commercially available in the market. The plants sprayed with the lowest concentration of the *Lupinus* polypeptide (100 µg native protein containing the polypeptide/mL; B) exhibit a lower level of development but still higher than that observed for the plants sprayed with water alone. The recommended level of application is therefore spraying the plants with a crude preparation of the *Lupinus* polypeptide containing 200 µg native protein containing the polypeptide/mL.

Example 9

Effect of spraying the native protein containing the polypeptide extracted from *Lupinus* on grapevine plants infected with *Uncinula necator* (the fungal causal agent of powdery mildew, economically the most important disease of grapevine worldwide).

A crude *Lupinus* extract was prepared containing 200 µg of the *Lupinus* native protein containing the polypeptide per mL. Grapevine plants infected with *Uncinula necator* and kept under greenhouse conditions were sprayed with the extract or with water (control). Twenty-four hours after application, the sprayed plants were observed—relative to the control, the plants sprayed with the *Lupinus* polypeptide exhibited a higher vigor and revealed the appearance of new shoots. This situation was maintained during at least one week, after which the plants, previously weakened by the presence of the fungus, were exuberant and with many new leaves with no symptom at all of the disease.

Example 10

Determination of the optimal calcium and magnesium concentrations required for the preparation of a tofu-type *Lupinus* native protein containing the polypeptide concentrate.

Figure 7:
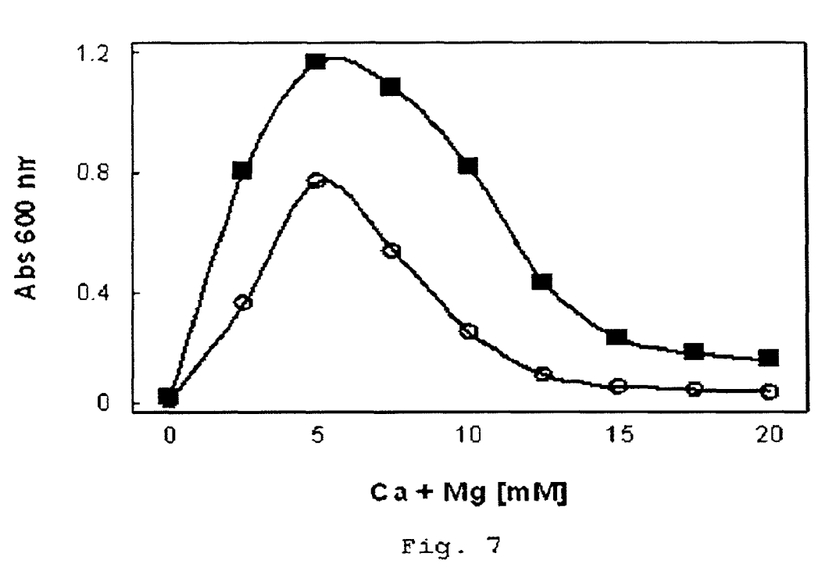
FIG. 7—Typical profile of the insolubility of the globulins from *Lupinus* genus plants as a function of calcium and magnesium concentrations. This profile is exemplified for the effect of these cations on the self-aggregation of the native protein containing the polypeptide extracted from *Lupinus* (■) and of β-conglutin from *Lupinus* (○). β-Conglutin (0.5 mg·mL$^{-1}$; ○) and the native protein containing the polypeptide extracted from *Lupinus* (0.5 mg·mL$^{-1}$; ■) were purified from dry seeds or from cotyledons detached from plantlets that were germinated and grown for eight days, respectively.

The well-balanced amino acid composition of the *Lupinus* native protein containing the polypeptide, as well as its excellent digestibility (the polypeptide is readily hydrolyzed into its component amino acids by the action of the human digestive tract proteases) highlight the great nutritive potential of the *Lupinus* polypeptide concentrate prepared after precipitation with 5 mM calcium+magnesium of the globulins present in a crude preparation of the *Lupinus* native protein containing the polypeptide (see FIG. 7).

REFERENCES

Fraley, R. T., Rogers, S. G., Horsch, R. B., Sanders, P. R., Flick, J. S., Adams, S. P., Bittner, M. L., Brand, L. A., Fink, C. L., Fry, J. S., Galluppi, G. R., Goldberg, S. B., Hoffman, N. L. & Woo, S. C. (1983). Expression of bacterial genes in plant cells. *Proceedings of the National Academy of Sciences USA,* 80, 4801-4807.

Ferreira, R. B., Franco, E. & Teixeira, A. R. (1999). Calcium- and magnesium-dependent aggregation of legume seed storage proteins. *Journal of Agricultural and Food Chemistry,* 47, 3009-3015.

Ferreira, R. B., Freitas, R. L. & Teixeira, A. R. (2003). Self-aggregation of legume seed storage proteins inside the protein storage vacuoles is electrostatic in nature, rather than lectin-mediated. *FEBS Letters,* 534, 106-110.

What is claimed is:

1. A transformed cell comprising a recombinant vector, wherein said vector comprises a DNA fragment comprising a nucleotide sequence encoding a polypeptide, the polypeptide comprising the amino acid sequence of SEQ ID NO:1 or a sequence having at least 85% sequence identity thereto,
wherein the polypeptide does not comprise a sequence of 531 consecutive amino acid residues of β conglutin from *Lupinus albus*, and
wherein the polypeptide exhibits at least one of the group consisting of: anti-fungal activity, anti-Oomycetes activity, insecticide activity, plant growth promoter activity, and nutritional properties.

2. The transformed cell of claim 1, wherein the cell is derived from *Escherichia coli*.

3. The transformed cell of claim 1, wherein the cell is derived from a plant or microorganism.

4. A transgenic plant comprising the transformed cell of claim 1, wherein the transgenic plant exhibits resistance to pathogenic fungi, Oomycetes or plagues caused by insects, being obtained by expression of the polypeptide in the transformed cell.

5. A method to produce a polypeptide, the polypeptide comprising the amino acid sequence of SEQ ID NO: 1 or a sequence having at least 85% sequence identity thereto,
wherein the polypeptide does not comprise a sequence of 531 consecutive amino acid residues of β conglutin from *Lupinus albus*, and
wherein the polypeptide exhibits at least one of the group consisting of: anti-fungal activity, anti-Oomycetes activity, insecticide activity, plant growth promoter activity, and nutritional properties,
the method comprising incubating a culture of the transformed cell of claim 1, and recovering the polypeptide from a cell culture or a cell extract.

* * * * *